United States Patent
Kuo (10) Patent No.: US 11,783,492 B2
(45) Date of Patent: Oct. 10, 2023

(54) HUMAN BODY PORTION TRACKING METHOD AND HUMAN BODY PORTION TRACKING SYSTEM

(71) Applicant: XRSPACE CO., LTD., Taoyuan (TW)

(72) Inventor: Sheng-Hsiu Kuo, Taipei (TW)

(73) Assignee: XRSPACE CO., LTD., Taoyuan (TW)

( * ) Notice: Subject to any disclaimer, the term of this patent is extended or adjusted under 35 U.S.C. 154(b) by 466 days.

(21) Appl. No.: 17/008,667

(22) Filed: Sep. 1, 2020

(65) Prior Publication Data

US 2022/0061700 A1     Mar. 3, 2022

(51) Int. Cl.
| | |
|---|---|
| *G06T 7/246* | (2017.01) |
| *A61B 5/00* | (2006.01) |
| *G06F 3/01* | (2006.01) |
| *G06T 7/215* | (2017.01) |
| *G06V 40/20* | (2022.01) |

(52) U.S. Cl.
CPC ............ G06T 7/246 (2017.01); A61B 5/0077 (2013.01); A61B 5/7425 (2013.01); G06F 3/011 (2013.01); G06T 7/215 (2017.01); G06V 40/28 (2022.01); *G06T 2207/30196* (2013.01); *G06T 2207/30241* (2013.01); *G06V 2201/07* (2022.01)

(58) Field of Classification Search
USPC ......................................................... 382/103
See application file for complete search history.

(56) References Cited

U.S. PATENT DOCUMENTS

| | | | | |
|---|---|---|---|---|
| 9,449,219 B2 * | 9/2016 | Bilet | .................. | G16Z 99/00 |
| 9,948,894 B2 * | 4/2018 | Brooks | .............. | H04L 12/1827 |
| 10,242,255 B2 | 3/2019 | Rafii et al. | | |
| 10,466,797 B2 * | 11/2019 | Song | .................... | G06F 3/0304 |
| 2014/0244344 A1 | 8/2014 | Bilet et al. | | |
| 2015/0062010 A1 * | 3/2015 | Lin | .................. | G06F 3/017 |
| | | | | 345/157 |
| 2017/0154471 A1 * | 6/2017 | Woo | .................. | G06T 7/75 |

(Continued)

FOREIGN PATENT DOCUMENTS

| | | |
|---|---|---|
| CN | 104424650 | 3/2015 |
| CN | 110263702 | 9/2019 |

(Continued)

OTHER PUBLICATIONS

Yamanaka et al. (A Parallel LSTM-based Missing Body Feature Point Completion in Video Frames Satoshi Yamanaka, Chonho Lee, Susumu Date DOI 10.1109/CSCI49370.2019.00121 2019 International Conference on Computational Science and Computational Intelligence (CSCI) pp. 646 to 651 © 2019 IEEE) (Year: 2019).*

(Continued)

*Primary Examiner* — Ishrat I Sherali (74) *Attorney, Agent, or Firm* — JCIP GLOBAL INC.

(57) ABSTRACT

A human body portion tracking method is provided and including obtaining a first image from an image capturing apparatus; identifying a first reference point and a second reference point from the first image; determining a position relationship between a first section and a second section of the human body portion according to three-dimensional coordinates of the first reference point and the second reference point; obtaining a second image from the image capturing apparatus; identifying a third reference point from the second image.

12 Claims, 5 Drawing Sheets

(56) References Cited

U.S. PATENT DOCUMENTS

2017/0285734 A1* 10/2017 Saito .................. H04N 5/23218
2020/0202538 A1*  6/2020 Hsu ........................ G06T 17/00
2023/0140030 A1*  5/2023 Pan ...................... G06V 10/761
                                                                382/103

FOREIGN PATENT DOCUMENTS

| EP | 2846308 A2 * | 3/2015 | ............ G06F 3/017 |
| TW | M369475 | 11/2009 | |
| TW | I464697 | 12/2014 | |
| TW | 201510771 | 3/2015 | |
| TW | I584644 | 5/2017 | |

OTHER PUBLICATIONS

"Search Report of Europe Counterpart Application", dated Mar. 16, 2021, p. 1-p. 8.

* cited by examiner

HUMAN BODY PORTION TRACKING METHOD AND HUMAN BODY PORTION TRACKING SYSTEM

BACKGROUND OF THE DISCLOSURE

1. Field of the Disclosure

The present disclosure generally relates to the motion prediction, in particular, to a human body portion tracking method and a human body portion tracking system.

2. Description of Related Art

Figure 1A:
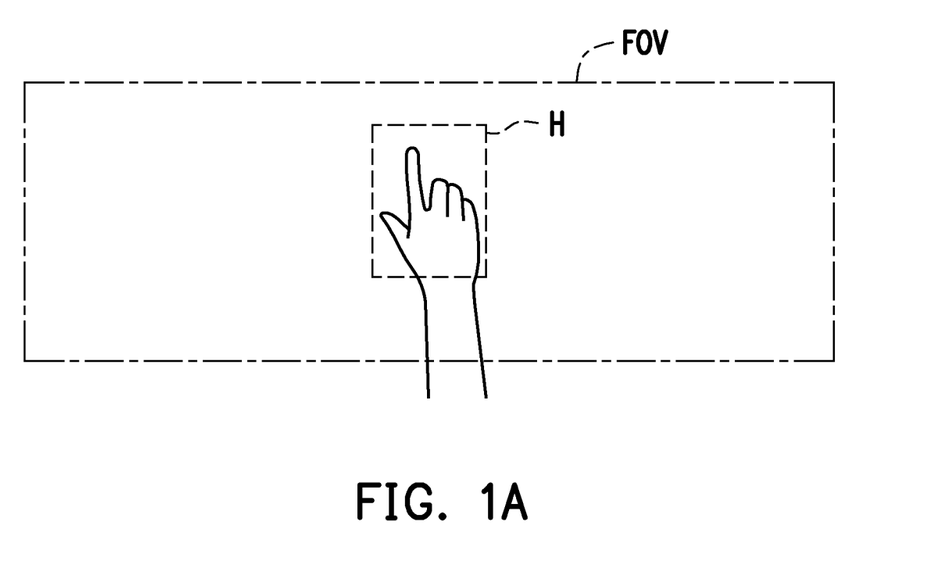
FIG. 1A and FIG. 1B are schematic diagrams illustrating an example of the motion of the hand.
Figure 1B:
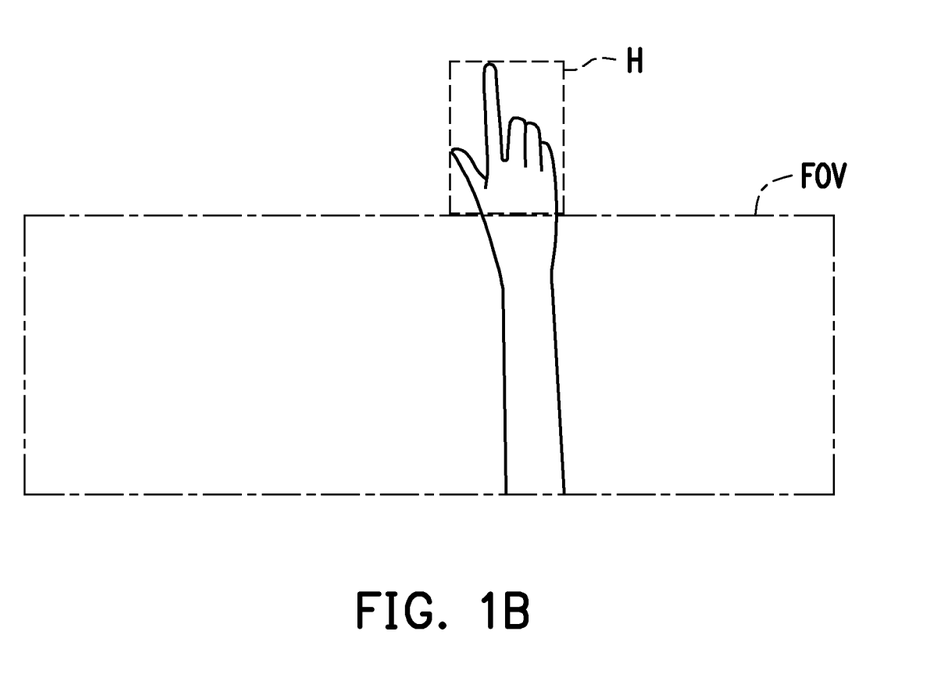

Technologies for simulating senses, perception, and/or environment, such as virtual reality (VR), augmented reality (AR), mixed reality (MR), and extended reality (XR), are popular nowadays. The aforementioned technologies can be applied in multiple fields, such as gaming, military training, healthcare, remote working, etc. In general, the user may wear a head mounted display to experience the virtual world. Furthermore, to provide intuitive operation on a head mounted display system, the motion of the user may be detected, to directly operate the head mounted display system according to the motion of the user. The motion of the user may be determined according to one or more images captured by the camera. However, the camera has a limitation of the field of view. For example, FIG. 1A and FIG. 1B are schematic diagrams illustrating an example of the motion of the hand. Referring to FIG. 1A, the hand H of the user is located within the field of view FOV of the camera. Referring to FIG. 1B, when the user further rises the hand H, the hand H may be located outside of the field of view FOV. The head mounted display system may not know the location of the hand H in FIG. 1B and not able to continue tracking the motion of the hand H.

SUMMARY OF THE DISCLOSURE

Accordingly, the present disclosure is directed to a human body portion tracking method and a human body portion tracking system, to predict the location of the missing part of the human body portion in the field of view of the camera.

In one of the exemplary embodiments, a human body portion tracking method includes, but not limited to, the following steps. A first image is obtained from an image capturing apparatus, where the first image captures a first section and a second section of a human body portion at a first time point. A first reference point and a second reference point are identified from the first image. The first reference point indicates the location of the first section at the first time point, and the second reference point indicates the location of a second section at the first time point. A position relationship between the first section and the second section is determined according to the three-dimensional coordinates of the first and second reference points. A second image is obtained from the image capturing apparatus. The second image captures the first section but not the second section at a second time point. A third reference point is identified from the second image. A third reference point from the second image is identified, where the third reference point indicates the location of the first section of the human body portion at the second time point. A three-dimensional coordinate of a fourth reference point is predicted by using a three-dimensional coordinate of the third reference point and the position relationship. The fourth reference point indicates the location of the second section of the human body portion at the second time point.

In one of the exemplary embodiments, a human body portion tracking system includes, but not limited to, an image capturing apparatus and a processor. The processor is coupled to the image capturing apparatus and configured for: obtaining a first image through the image capturing apparatus, where the first image captures a first section and a second section of a human body portion at a first time point, and the first section of the human body portion connects to the second section of the human body portion; identifying a first reference point and a second reference point from the first image, where the first reference point indicates the location of the first section of the human body portion at the first time point, and the second reference point indicates the location of a second section of the human body portion at the first time point; determining a position relationship between the first section and the second section of the human body portion according to three-dimensional coordinates of first reference point and the second reference point; obtaining a second image through the image capturing apparatus, where the second image captures the first section but not the second section of the human body portion at a second time point; identifying a third reference point from the second image, where the third reference point indicates the location of the first section of the human body portion at the second time point; and predicting a three-dimensional coordinate of a fourth reference point by using a three-dimensional coordinate of the third reference point and the position relationship, where the fourth reference point indicates the location of the second section of the human body portion at the second time point; and determining a position relationship between the first section and the second section according to the first image.

It should be understood, however, that this Summary may not contain all of the aspects and embodiments of the present disclosure, is not meant to be limiting or restrictive in any manner, and that the invention as disclosed herein is and will be understood by those of ordinary skill in the art to encompass obvious improvements and modifications thereto.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DESCRIPTION OF THE EMBODIMENTS

Reference will now be made in detail to the present preferred embodiments of the disclosure, examples of which are illustrated in the accompanying drawings. Wherever possible, the same reference numbers are used in the drawings and the description to refer to the same or like parts.

Figure 2:
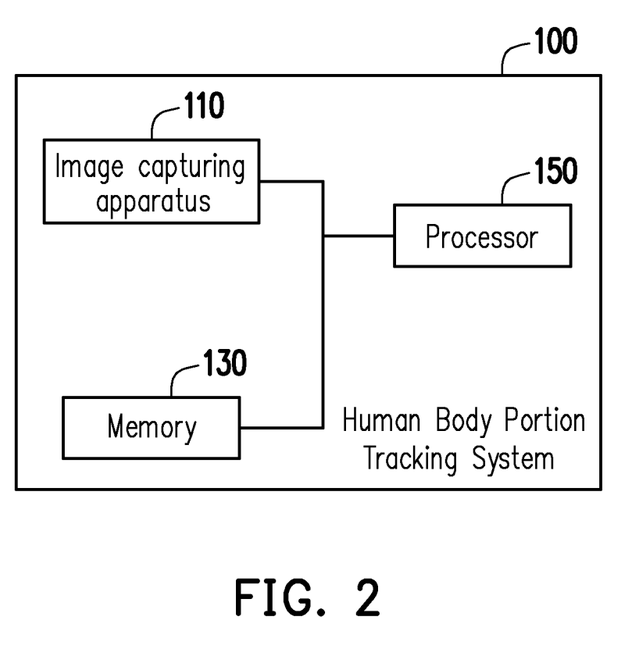
FIG. 2 is a block diagram illustrating a human body portion tracking system according to one of the exemplary embodiments of the disclosure.

FIG. 2 is a block diagram illustrating a human body portion tracking system 100 according to one of the exemplary embodiments of the disclosure. Referring to FIG. 2, the human body portion tracking system 100 includes, but not limited to, an image capturing apparatus 110, a memory 130, and a processor 150. The human body portion tracking system 100 is adapted for VR, AR, MR, XR, or other reality simulation related technologies.

The image capturing apparatus 110 may be a camera, such as a monochrome camera or a color camera, a deep camera, a video recorder, or other image sensors capable of capturing images. In one embodiment, the image capturing device 120 is disposed on the main body of the head mounted display (HMD) and captures toward a specific direction. For example, when the user wears the HMD, the image capturing apparatus 110 captures the scene in front of the user. In some embodiments, the direction and/or the field of view of the image capturing apparatus 110 could be adjusted based on actual requirement. In still some embodiments, the image capturing apparatus 110 may be used to capture toward one or more human body portions of the user, to generate image including human body portions of the user. For example, one or more human body portions may include hands, arms, ankles, legs, or other human body portions of the user.

The memory 130 may be any type of a fixed or movable random-access memory (RAM), a read-only memory (ROM), a flash memory, a similar device, or a combination of the above devices. The memory 130 records program codes, device configurations, buffer data, or permanent data (such as images, locations, position relationship, three-dimensional coordinates, and motion model), and these data would be introduced later.

The processor 150 is coupled to the image capturing apparatus 110 and the memory 130. The processor 150 is configured to load the program codes stored in the memory 130, to perform a procedure of the exemplary embodiment of the disclosure.

In some embodiments, the processor 150 may be a central processing unit (CPU), a microprocessor, a microcontroller, a digital signal processing (DSP) chip, a field-programmable gate array (FPGA). The functions of the processor 150 may also be implemented by an independent electronic device or an integrated circuit (IC), and operations of the processor 150 may also be implemented by software.

It should be noticed that the processor 150 may not be disposed at the same apparatus with the image capturing apparatus 110. However, the apparatuses respectively equipped with the image capturing apparatus 110 and the processor 150 may further include communication transceivers with compatible communication technology, such as Bluetooth, Wi-Fi, and IR wireless communications, or physical transmission line, to transmit or receive data with each other. For example, the processor 150 may be disposed in a computing device while the image capturing apparatus 110 being disposed on the main body of the HMD.

To better understand the operating process provided in one or more embodiments of the disclosure, several embodiments will be exemplified below to elaborate the operating process of the human body portion tracking system 100. The devices and modules in the human body portion tracking system 100 are applied in the following embodiments to explain the control method provided herein. Each step of the method can be adjusted according to actual implementation situations and should not be limited to what is described herein.

Figure 3:
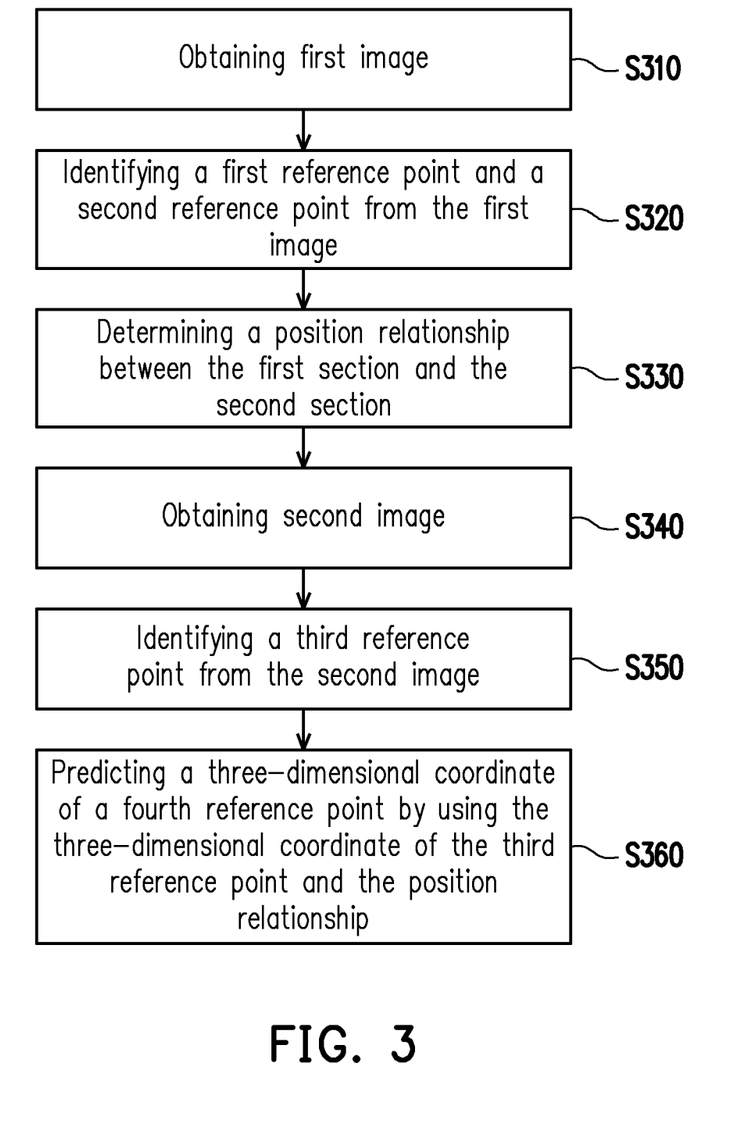
FIG. 3 is a flowchart illustrating a human body portion tracking method according to one of the exemplary embodiments of the disclosure.

FIG. 3 is a flowchart illustrating a human body portion tracking method according to one of the exemplary embodiments of the disclosure. Referring to FIG. 3, the processor 150 may obtain a first image through/from the image capturing apparatus 110 (step S310). Specifically, the first image is one of the images captured by the image capturing apparatus 110 at the first time point. It should be noticed that the first image captures a first section and a second section of a human body portion at a first time point. That is, the first and second sections of the human body portion are both located within the field of view of the image capturing apparatus 110. The human body portion could be a hand, an arm, a leg, foot, an ankle, a leg, or other human body portions of the user. The first section of the human body portion connects to the second section of the human body portion. The first and second sections maybe the parts of the human body portion between joints or any two neighboring parts of the human body portion. For example, the first section is the forearm, and the second section is the hand. For another example, the first section is the palm, and the second section is one finger. In some embodiment, the sections are determined based on the actual requirements. The processor 150 may further identify the human body portion, the first section, and the second section in the first image through a machine learning technology (such as deep learning, artificial neural network (ANN), or support vector machine (SVM), etc.) configured with object recognition function or other image recognition technologies.

The processor 150 may identify a first reference point and a second reference point from the first image (step S320). In one embodiment, the first reference point indicates the location of the first section of the human body portion at the first time point, and the second reference point indicates the location of the second section of the human body portion at the first time point. The first reference point and the second reference point could be the barycenters, the geometric centers, or any points located at the first section and the second section, respectively. In some embodiments, more reference points, a surface, the outline can be used to indicate the location of the first or second section.

Figure 4:
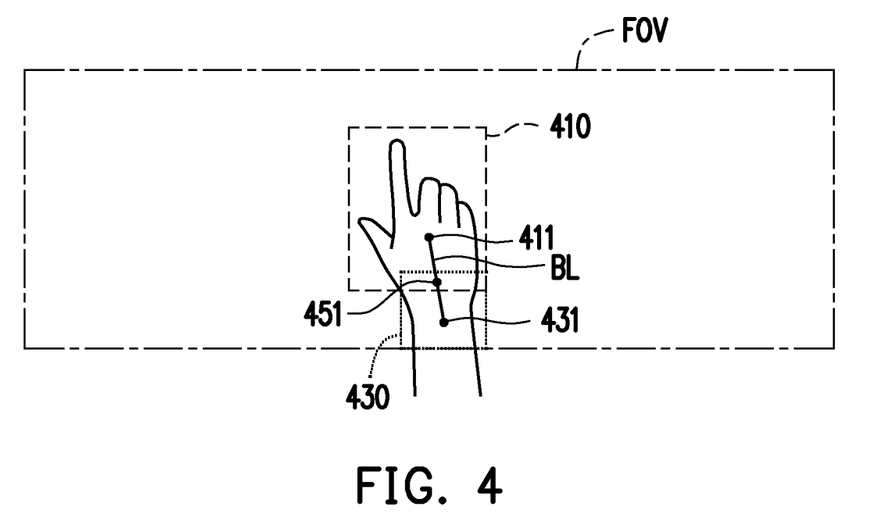
FIG. 4 is a schematic diagram illustrating the motion of a human body portion at a first time point according to one of the exemplary embodiments of the disclosure.

FIG. 4 is a schematic diagram illustrating the motion of a human body portion at a first time point according to one of the exemplary embodiments of the disclosure. Referring to FIG. 4, at the first time point, the hand 410 and the forearm 430 are both located within the field of view FOV. Furthermore, the processor 150 determine one point located at the forearm 430 and the barycenter of the hand 410 as the first reference point 431 and the second reference point 411, respectively.

The processor 150 may determine the position relationship between the first section and the second section of the human body portion according to the three-dimensional coordinates of first reference point and the second reference point (step S330). Specifically, the three-dimensional coordinates is one of format to represent the location of a point in a space. The sensing strengths and the pixel positions corresponding to the first reference point and the second reference point in the first image can be used for estimating depth information of the first reference point and the second reference point (i.e., a distance relative to the image capturing apparatus 110 or other reference apparatuses) and estimating two-dimensional coordinates of the first reference point and the second reference point at a plane parallel to the image capturing apparatus 110, so as to generate the three-dimensional coordinates of the first reference point and the second reference point. In some embodiment, the relative location or the depth could be used to represent the location of a point.

Furthermore, the position relationship is related to the relative position between the first and second sections of the human body portion. For example, the distance between the first and second sections and/or the direction from the first section to the second section.

In one embodiment, the processor 150 may connect the first reference point of the first section and the second reference point of the second section in the first image, to form a body link between the first reference point and the second reference point as the position relationship. Taking FIG. 4 as an example, the body link BL connects the first reference point 431 and the second reference point 411. That is, the first reference point 431 and the second reference point 411 are two ends of the body link BL.

In some embodiments, the body link BL may not be a straight line. An intersection point 451 may be generated between the hand 410 and the forearm 430. For example, the intersection point 451 is located at the wrist. Furthermore, the body link BL may further pass through the intersection point 451.

The processor 150 may obtain a second image through/from the image capturing apparatus 110 (step S340). Specifically, the second image is another one of the images captured by the image capturing apparatus 110 at a second time point after the first time point. It should be noticed that the second image captures the first section but not the second section at the second time point. That is, the human body portion moves, and merely the first section of the human body portion is located within the field of view of the image capturing apparatus 110.

The processor 150 may identify a third reference point from the second image (step S350). In one embodiment, the third reference point indicates the location of the first section of the human body portion at the second time point. The third reference point could be the barycenters, the geometric centers, or any points located at the first section. In some embodiments, more reference points, a surface, the outline can be used to indicate the location of the first section at the second time point.

Figure 5:
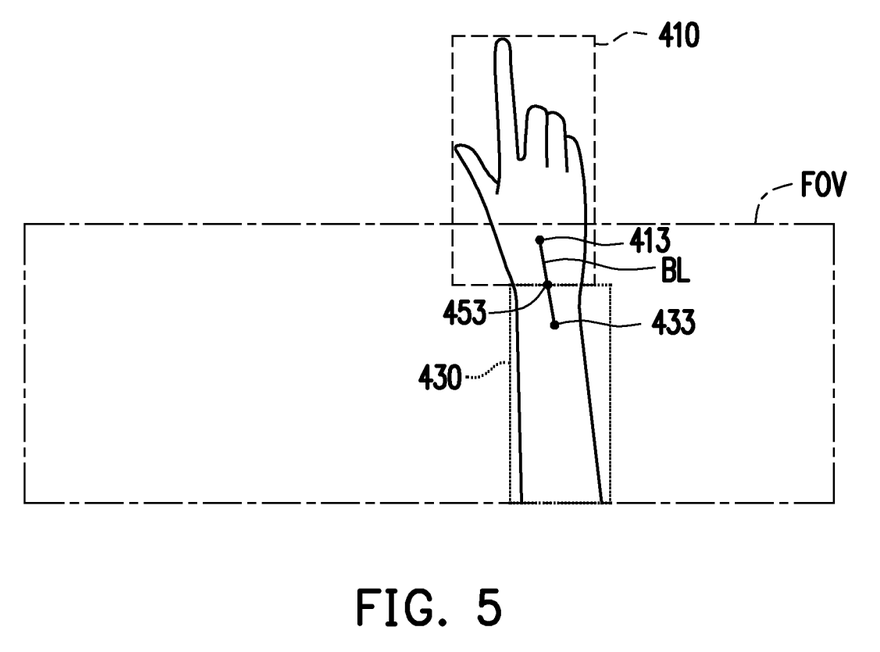
FIG. 5 is a schematic diagram illustrating the motion of the human body portion at a second time point according to one of the exemplary embodiments of the disclosure.

FIG. 5 is a schematic diagram illustrating the motion of the human body portion at a second time point according to one of the exemplary embodiments of the disclosure. Referring to FIG. 5, at the second time point, merely the forearm 430 is located within the field of view FOV, and the hand 410 is located outside of the field of view FOV. Furthermore, the processor 150 determines the one point located at the forearm 430 as the third reference point 433.

The processor may predict the three-dimensional coordinate of a fourth reference point by using the three-dimensional coordinate of the third reference point and the position relationship (step S360). In one embodiment, the fourth reference point indicates the location of the second section of the human body portion at the second time point. The fourth reference point could be the barycenters, the geometric centers, or any points located at the second section. In some embodiments, more reference points, a surface, the outline can be used to indicate the location of the second section at the second time point.

Because the fourth reference point may be not located within the field of view, the processor 150 can not determine the location of the second section based on the second image as the location of the first section directly. It is assumed the position relationship is related to the location of the third reference point and the location of the fourth reference point. The relative position between the first and the second sections at the first time point may be still the same as the relative position between the first and the second sections at the second time point.

In one embodiment, the processor 150 may determine the three-dimensional coordinate of the fourth reference point by connecting the third reference point and the fourth reference point in the second image along with the body link. The body link may retain its shape. However, the two ends of the body link would be changed to the third reference point and the fourth reference point from the first reference point and the second reference point. The processor 150 may determine the coordinate difference between the first reference point and the second reference point based on the body link, and use the three-dimensional coordinate of the third reference point and the coordinate difference to determine the three-dimensional coordinate of the fourth reference point.

Taking FIG. 4 and FIG. 5 as an example, the body link BL may shift along with the motion of the hand 410 and the forearm 430. There would be the body link BL connecting the third reference point 433, (the third reference point 453) and the fourth reference point 413. Accordingly, the location of the fourth reference point 413 can be determined.

In one embodiment, the processor 150 may determine a base point located at the end of the first section but not located at the second section. For example, the first section is the forearm, the second section is the hand, and the base point is located at the elbow. The processor 150 may estimate the location of a target point located at the second section according to the locations of a middle point located between the first section and the second section and the base point in the second image based on inverse kinematics. Taking the elbow as the base point for example, the middle point may be located at the wrist which is the intersection of the forearm and the hand, and the target point may be the end of the finger. On the other hand, the inverse kinematics is a mathematical process of calculating parameters of joints. The processor 150 may consider the middle point, the base point, and the target point as the joints for the inverse kinematics. Based on the inverse kinematics, given joint parameters (such as the angle between the first section and the second section, the locations of the base point and the middle point, etc.), the location of the target point can be estimated. Then, the processor 150 may adjust the three-dimensional coordinate of the fourth reference point according to the location of the target point. It is assumed the fourth reference point and the target point are both located at the second section of the human body portion. The processor 150 may use the target point to check whether the fourth reference point deviates from a corrected location and further modify the three-dimensional coordinate of the fourth reference point.

Figure 6:
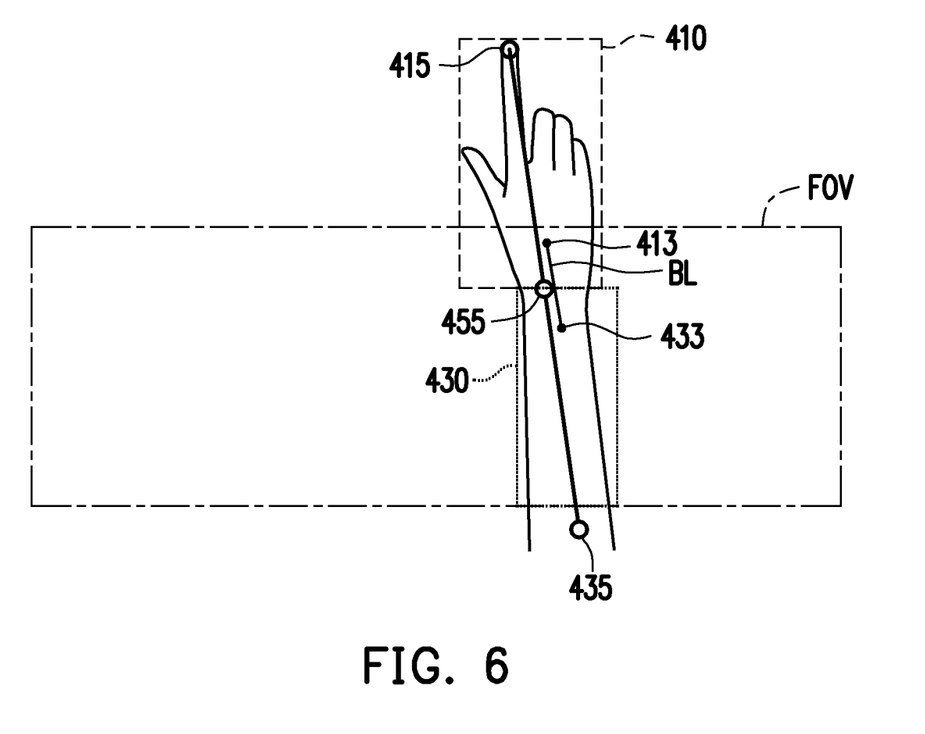
FIG. 6 is a schematic diagram illustrating the motion of the human body portion at the second time point according to one of the exemplary embodiments of the disclosure.

FIG. 6 is a schematic diagram illustrating the motion of the human body portion at the second time point according to one of the exemplary embodiments of the disclosure. Referring to FIG. 6, the base point 435 is located at the elbow, the middle point 455 is located at the wrist, and the target point 415 is located at the end of the finger. The location of the target point 415 can be determined based on the base point 435 and the middle point 455 by using inverse kinematics. The processor 150 may determine whether the fourth reference point is located at a line connecting the middle point 455 and the target 415. The processor 150 may further modify the three-dimensional coordinate of the fourth reference point 413 based on the line of the middle point 455 and the target 415.

In one embodiment, the processor 150 may determine the motion model of the second section according to the first image and one or more previous images. The one or more previous images are obtained from the image capturing apparatus 110 before the first image. The processor 150 may analyze the displacement of the second section among the first image and the previous image, and further estimate the trajectory, rotation, and/or speed of the second section. On the other hand, the motion model is a mathematical model that simulates the motion of the second section. The trajectory, rotation, and/or speed of the second section can be used to estimate the motion model. For example, if the speed remains fixed value, the motion model may be a constant velocity motion. The processor 150 may further adjust the three-dimensional coordinate of the fourth reference point according to the motion model. For example, if the motion model is the rotating motion, the location of the fourth reference point may be lowered.

In one embodiment, the processor 150 may adjust the three-dimensional coordinate of the fourth reference point based on the motion model according to the location of the target point. That is, the processor 150 may use the location of the target point to further adjust the modified three-dimensional coordinate of the fourth reference point based on the motion model. For example, the processor 150 determines whether the modified three-dimensional coordinate of the fourth reference point is located at the line connecting the middle point and the target point. Accordingly, the accuracy of location estimation may be improved.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims and their equivalents.

What is claimed is:

1. A human body portion tracking method, comprising:
    obtaining a first image from an image capturing apparatus, wherein the first image captures a first section and a second section of a human body portion at a first time point, and the first section of the human body portion connects to the second section of the human body portion;
    identifying a first reference point and a second reference point from the first image, wherein the first reference point indicates a location of the first section of the human body portion at the first time point, and the second reference point indicates a location of the second section of the human body portion at the first time point;
    determining a position relationship between the first section and the second section of the human body portion according to three-dimensional coordinates of first reference point and the second reference point;
    obtaining a second image from the image capturing apparatus, wherein the second image captures the first section but not the second section of the human body portion at a second time point;
    identifying a third reference point from the second image, wherein the third reference point indicates a location of the first section of the human body portion at the second time point; and
    predicting a three-dimensional coordinate of a fourth reference point by using a three-dimensional coordinate of the third reference point and the position relationship, wherein the fourth reference point indicates a location of the second section of the human body portion at the second time point.

2. The human body portion tracking method according to claim 1, wherein the step of determining the position relationship between the first section and the second section comprises:
    connecting the first reference point of the first section and the second reference point of the second section in the first image, to form a body link between first reference point and the second reference point as the position relationship.

3. The human body portion tracking method according to claim 2, wherein the step of predicting the three-dimensional coordinate of the fourth reference point comprises:
    determining the three-dimensional coordinate of the fourth reference point by connecting the third reference point and the fourth reference point in the second image along with the body link.

4. The human body portion tracking method according to claim 3, further comprising:
    determining a base point located at an end of the first section at the second time point; and
    estimating a location of a target point located at the second section according to the locations of a middle point located between the first section and the second section and the base point in the second image based on inverse kinematics, wherein the inverse kinematics is a mathematical process of calculating parameters of joints, and the middle point, the base point, and the target point are considered as the joints; and
    adjusting the three-dimensional coordinate of the fourth reference point according to the location of the target point.

5. The human body portion tracking method according to claim 3, further comprising:
    determining a motion model of the second section according to the first image and at least one previous image, wherein the at least one previous image is obtained before the first image, and the motion model is a mathematical model which simulates motion of the second section; and
    adjusting the three-dimensional coordinate of the fourth reference point according to the motion model.

6. The human body portion tracking method according to claim 5, further comprising:
    determining a base point located at an end of the first section at the second time point; and
    estimating a location of a target point located at the second section according to the locations of a middle point located between the first section and the second section and the base point in the second image based on inverse kinematics, wherein the inverse kinematics is a mathematical process of calculating parameters of joints, and the base point, the middle point and the target point are considered as the joints; and
    adjusting the three-dimensional coordinate of the fourth reference point based on the motion model according to the location of the target point.

7. A human body portion tracking system, comprising:

an image capturing apparatus;

a processor, coupled to the image capturing apparatus, and configured for:

obtaining a first image through the image capturing apparatus, wherein the first image captures a first section and a second section of a human body portion at a first time point, and the first section of the human body portion connects to the second section of the human body portion;

identifying a first reference point and a second reference point from the first image, wherein the first reference point indicates a location of the first section of the human body portion at the first time point, and the second reference point indicates a location of the second section of the human body portion at the first time point;

determining a position relationship between the first section and the second section of the human body portion according to three-dimensional coordinates of first reference point and the second reference point;

obtaining a second image through the image capturing apparatus, wherein the second image captures the first section but not the second section of the human body portion at a second time point;

identifying a third reference point from the second image, wherein the third reference point indicates a location of the first section of the human body portion at the second time point; and predicting a three-dimensional coordinate of a fourth reference point by using a three-dimensional coordinate of the third reference point and the position relationship, wherein the fourth reference point indicates a location of the second section of the human body portion at the second time point.

8. The human body portion tracking system according to claim 7, wherein the processor is configured for:

connecting the first reference point of the first section and the second reference point of the second section in the first image, to form a body link between first reference point and the second reference point as the position relationship.

9. The human body portion tracking system according to claim 8, wherein the processor is configured for:

determining the three-dimensional coordinate of the fourth reference point by connecting the third reference point and the fourth reference point in the second image along with the body link.

10. The human body portion tracking system according to claim 9, wherein the processor is configured for:

determining a base point located at an end of the first section at the second time point; and estimating a location of a target point located at the second section according to the locations of a second feature point and the base point in the second image based on inverse kinematics, wherein the inverse kinematics is a mathematical process of calculating parameters of joints, and the middle point, the base point and the target point are considered as the joints; and adjusting the three-dimensional coordinate of the fourth reference point according to the location of the target point.

11. The human body portion tracking system according to claim 9, wherein the processor is configured for:

determining a motion model of the second section according to the first image and at least one previous image, wherein the at least one previous image is obtained before the first image, and the motion model is a mathematical model which simulates motion of the second section; and adjusting three-dimensional coordinate of the fourth reference point according to the motion model.

12. The human body portion tracking system according to claim 11, wherein the processor is configured for:

determining a base point located at an end of the first section at the second time point; and estimating a location of a target point located at the second section according to the locations of a middle point located between the first section and the second section and the base point in the second image based on inverse kinematics, wherein the inverse kinematics is a mathematical process of calculating parameters of joints, and the middle point, the target point and the base point are considered as the joints; and adjusting the three-dimensional coordinate of the fourth reference point based on the motion model according to the location of the target point.

* * * * *